United States Patent [19]

Prosen

[11] 4,255,190
[45] Mar. 10, 1981

[54] ESSENTIALLY NON-PRECIOUS STAINLESS DENTAL ALLOY

[75] Inventor: Emil M. Prosen, Bala-Cynwyd, Pa.

[73] Assignee: Neoloy Products, Inc., Posen, Ill.

[21] Appl. No.: 88,037

[22] Filed: Oct. 25, 1979

[51] Int. Cl.³ .............................................. C22C 19/07
[52] U.S. Cl. .................................... 75/134 C; 75/171
[58] Field of Search .............................. 75/134 C, 171

[56] References Cited

U.S. PATENT DOCUMENTS 3,134,670  5/1964  Prosen ..................................... 75/171

Primary Examiner—R. Dean
Attorney, Agent, or Firm—Jacobs & Jacobs

[57] ABSTRACT

The present invention provides an essentially non-precious stainless dental alloy which may be used in producing crowns, bridges, inlays, and the like. It also provides an alloy which is especially adapted for the application of low fusing opaqueing porcelain for adhesion to such dental appliances. The alloy of the present invention has a melting point approximating 2650° F. In its broadest aspect the alloy consists of cobalt 40 to 60%, chromium 25 tp 32%, tungsten 7 to 15%, ruthenium 1 to 5%, gallium 1 to 5%, niobium 0.5 to 2%, copper 0.5 to 2%, tantalum 0.5 to 1%, silicon 0.5 to 1%, iron 0.5 to 1%. While ruthenium is of the platinum group of elements, it is included in such a small amount as to make the alloy essentially of non-precious stainless metals.

3 Claims, No Drawings

ESSENTIALLY NON-PRECIOUS STAINLESS DENTAL ALLOY

The present invention relates to an essentially non-precious stainless alloy especially adapted for use in the dental field for the preparation of crowns, bridges, inlays, and other dental prostheses to which it is desired to apply a porcelain surface. The principal advantage of the alloy of the present invention is that it provides an alloy to which a low-fusing porcelain can be adhered by fusion.

It is also an economy alloy in that it does not contain any of the higher priced metals such as gold and platinum, although it does contain a small amount of ruthenium which is of the platinum group of elements.

BACKGROUND OF THE INVENTION

In the dental field it is now well recognized that the alloy to which low-fusing porcelain can be successfully applied so as to have complete adhesion must be compatible from the standpoint of coefficient of linear expansion and contraction at the fusing temperature of the porcelain; and that such alloy must provide on its surface oxides which facilitate the adhesion of the porcelain.

It is also well understood that after application of the porcelain to the alloy, the porcelain surface should not check, crack or separate from the base alloy.

There are on the market today various opaque porcelains which are especially prepared and sold for application to dental alloys. The opaqueing materials of such opaque porcelains vary from one to the other and the basic ingredients of such opaque porcelains are not fully disclosed in any literature with which I am familiar. Essentially all opaque porcelains for dental application are said to be low-fusing in that they will fuse at a temperature of about 1800° F. to dental alloys and will adhere to the same provided all other conditions are met for fusing such porcelains to the metal alloy.

PRIOR ART

Applicant is the inventor of U.S. Pat. No. 4,046,561 dated Sept. 6, 1977. This patent discloses and claims a wholly different dental alloy for use in the adhesion of porcelain.

Applicant is also inventor of U.S. Pat. No. 4,124,382 dated Nov. 7, 1978 which discloses and claims another dental alloy for use in the adhesion of porcelain.

Applicant is also the inventor of U.S. patent application Ser. No. 6,078, filed Jan. 24, 1979, allowed June 18, 1979, which discloses and claims another dental alloy for use in the adhesion of porcelain. The references made of record in each of these patents and patent application are not believed to be anticipatory of the present invention.

Applicant is also the inventor of the following U.S. patent applications: Application Ser. No. 051,003, filed June 22, 1979; and Application Ser. No. 71,128, filed Aug. 30, 1979.

Applicant submits that none of his prior patents and co-pending patent applications, teach or suggest the dental alloy invention herein sought to be patented.

SUMMARY OF THE INVENTION

According to the present invention, and after considerable experimental work, I have found that an essentially non-precious stainless dental alloy consisting of the following elements in its preferred form can be fused to all opaque porcelains with which I am familiar, with excellent results. The preferred formulation for such an alloy is:

| | |
|---|---|
| Cobalt | 53% |
| Chromium | 27% |
| Tungsten | 10% |
| Ruthenium | 3% |
| Gallium | 3% |
| Niobium | 1% |
| Copper | 1% |
| Tantalum | 1% |
| Silicon | 0.5% |
| Iron | 0.5% |

According to tests which I have conducted, I can state that an alloy of this preferred formulation has the following mechanical characteristics:

Melting Point 2650° F.

Thermal coefficient of expansion $1.43 \times 10^{-5}$ per °C.

DETAILED DESCRIPTION OF THE INVENTION

Supplementing what is set forth above under the heading of "Summary of the Invention", I have found that an alloy chiefly consisting of cobalt, chromium and tungsten, with the other elements in small quantities as set forth above, is ideally suited for fusing at approximately 1800° F. with opaque porcelains. I have also found that after fusing and cooling, such porcelains are so adherent to the alloy that it is impossible to separate the same with repeated hammer blows.

In the broader aspect of the invention I have found that the various elements constituting the alloy may vary within the following ranges:

| | |
|---|---|
| Cobalt | 40% to 60% |
| Chromium | 25% to 32% |
| Tungsten | 7% to 15% |
| Ruthenium | 1% to 5% |
| Gallium | 1% to 5% |
| Niobium | 0.5% to 2% |
| Copper | 0.5% to 2% |
| Tantalum | 0.5% to 1% |
| Silicon | 0.5% to 1% |
| Iron | 0.5% to 1% |

In my earlier application, Ser. No. 051,003, filed June 22, 1979, I have disclosed a non-precious stainless dental alloy which in its preferred formulation consists of: cobalt 52%; chromium 28%; tungsten 12%; gallium 4%; copper 1%; niobium 1%; silicon 0.5%; and iron 1.5%;.

In the preferred formulation of the alloy of the present invention, I have added 3% ruthenium and 1% tantalum. Neither of these elements were included in the formulation of my application Ser. No. 051,003.

As set forth above, the preferred form of the alloy of this application has a melting temperature of 2650° F. as distinguished from 2550° F. of my earlier application. Also, the linear coefficient of expansion of the present alloy is $1.43 \times 10^{-5}$ per °C. as compared with the linear coefficient of expansion of $1.49 \times 10^{-5}$ per °C. as set forth in my earlier application.

I have found that the dental alloy of the present invention is compatible with all low fusing opaque porcelain materials. From my experimentation I attribute this compatibility to the presence of ruthenium in the percentage set out in the preferred formula.

It is well understood in the art that surface oxides must be formed on the alloy in order to promote and assure adhesion by fusion of the opaque porcelain. It is also well understood in the art that the coefficient of expansion and contraction of the alloy must be compatible with the coefficient of expansion and contraction of the low fusing porcelains so as to avoid checking, cracking or separation of the same from the base metal alloy. Some porcelains are known to have a higher coefficient of expansion while others are known to have a lower coefficient of expansion. The alloy of the present invention is intended primarily for use with low fusing porcelain having a lower coefficient of expansion as will be apparent from the fact that in the preferred formulation the alloy of the present invention has a $1.43 \times 10^{-5}$ per °C. coefficient of expansion compared to the $1.43 \times 10^{-5}$ per °C. coefficient of expansion of my earlier application Ser. No. 051,003, filed June 22, 1979.

While ruthenium is a metal of the platinum group of elements which normally do not oxidize when subjected to heat, I have found that oxides start to form on ruthenium at approximately 800° F. Some of the other elements forming part of the present dental alloy form oxides at lower temperatures.

When the cast metal restoration is ready for opaque porcelain application, it is brought up to a temperature of 1800° F. which is the normal temperature for low fusing porcelain application, as well understood in the art. I have observed that during the period of bringing the cast dental restoration up to this temperature for application of the porcelain, at approximately 800° F. ruthenium oxidizes on its surface in addition to the other lower temperature oxidizing materials of the alloy. Hence there is provided on the surface of the dental metal restoration, oxides including the ruthenium oxide which provide a very strong adhesion of the porcelain to the base metal.

In the preparation of the alloy of the present invention I have observed that the small amount of ruthenium has a very beneficial effect on the linear coefficient of expansion, in that the metal in its final cast form seems to solidify denser—thus reducing the coefficient of expansion of the dental alloy in the final form and making the alloy more compatible with the lower linear coefficient of expansion of certain low fusing porcelains. I have also observed that the addition of ruthenium improves corrosion resistance in the alloy.

It will be noted that in this alloy as contrasted with the alloy of my co-pending application, Ser. No. 051,003 filed June 22, 1979, a small amount of tantalum (1% in the preferred form) is added. I have found this small amount of tantalum serves to reduce the melting point of the alloy to bring it to its preferred melting temperature of 2650° F. Alloys which melt beyond this temperature have been found to be difficult to work with in normal dental operations.

It will thus be understood that the important advantages of the present alloy, as contrasted with the prior art set forth herein, is the presence of ruthenium and tantalum in the small amounts set forth.

What I claim is:

1. An essentially non-precious stainless alloy especially adapted for the adhesion of opaqueing porcelain having a fusing temperature of approximately 1800° F., consisting of:

| | |
|---|---|
| Cobalt | 40% to 60% |
| Chromium | 25% to 32% |
| Tungsten | 7% to 15% |
| Ruthenium | 1% to 5% |
| Gallium | 1% to 5% |
| Niobium | 0.5% to 2% |
| Copper | 0.5% to 2% |
| Tantalum | 0.5% to 1% |
| Silicon | 0.5% to 1% |
| Iron | 0.5% to 1% | said alloy having a melting temperature of approximately 2650° F., and a linear coefficient of expansion of about $1.4 \times 10^{-5}$ per °C.

2. An essentially non-precious stainless alloy consisting of:

| | |
|---|---|
| Cobalt | 53% |
| Chromium | 27% |
| Tungsten | 10% |
| Ruthenium | 3% |
| Gallium | 3% |
| Niobium | 1% |
| Copper | 1% |
| Tantalum | 1% |
| Silicon | 0.5% |
| Iron | 0.5% |

3. An essentially non-precious stainless alloy according to claim 2, especially adapted for adhesion to opaqueing porcelain having a fusing temperature of approximately 1800° F., said dental alloy having a melting temperature of approximately 2650° F. and a linear coefficient of expansion of approximately $1.43 \times 10^{-5}$ per ° C.

* * * * *

UNITED STATES PATENT AND TRADEMARK OFFICE
CERTIFICATE OF CORRECTION

PATENT NO. : 4,255,190
DATED : March 10, 1981
INVENTOR(S) : EMIL M. PROSEN

It is certified that error appears in the above-identified patent and that said Letters Patent are hereby corrected as shown below:

ABSTRACT

Line 9, after "25" change "tp" to --- to ---

SPECIFICATION

Column 3, line 19, change "1.43" to --- 1.49 ---

Signed and Sealed this

Ninth Day of June 1981

[SEAL]

Attest:

RENE D. TEGTMEYER

Attesting Officer    Acting Commissioner of Patents and Trademarks